United States Patent [19]
Guering et al.

[11] Patent Number: 5,602,648
[45] Date of Patent: Feb. 11, 1997

[54] PROCESS AND DEVICE FOR MEASURING OPTICAL QUALITY OF THE SURFACE OF A TRANSPARENT OBJECT BY CONTACT WITH A WETTED FLEXIBLE SURFACE

[75] Inventors: Paul H. Guering, Paris; Patrick Gayout, Gagny, both of France

[73] Assignee: Saint Gobain Vitrage, Courbevoie, France

[21] Appl. No.: 414,598

[22] Filed: Aug. 31, 1995

[30] Foreign Application Priority Data

Mar. 31, 1994 [FR] France .................................. 94 03831

[51] Int. Cl.⁶ .......................... G01N 21/55; G01N 21/00
[52] U.S. Cl. .................... 356/445; 356/239; 356/430; 356/128
[58] Field of Search .............................. 356/128, 239, 356/371, 445, 448, 430–431

[56] References Cited

U.S. PATENT DOCUMENTS

| | | | |
|---|---|---|---|
| 2,660,916 | 12/1953 | Zobel et al. | 356/371 |
| 4,049,350 | 9/1977 | Brück | 356/239 |
| 4,152,069 | 5/1979 | Brück | 356/239 |
| 4,645,337 | 2/1987 | Obenreder | 356/239 |
| 5,146,282 | 9/1992 | Guering et al. | 356/239 |

FOREIGN PATENT DOCUMENTS 0463940  1/1992  European Pat. Off. .

OTHER PUBLICATIONS

Patent Abstracts of Japan, vol. 17, No. 536 (P–1620), Sep. 27, 1993, JP–A–149732, Jun. 15, 1993.
Patent Abstracts of Japan, vol. 12, No. 199 (P–714), Jun. 9, 1988, JP–A–63 001909, Jan. 6, 1988.

*Primary Examiner*—Frank Gonzalez
*Assistant Examiner*—Jason D. Eisenberg
*Attorney, Agent, or Firm*—Oblon, Spivak, McClelland, Maier & Neustadt, P.C.

[57] ABSTRACT

In order to measure the optical quality of the surface of a transparent sheet, the second surface of the sheet is placed in contact with a flexible material which is wetted with an index liquid. In the case of soda lime glass, water is suitable. The optical measurement can be carried out by traditional methods, ombroscopy in particular.

8 Claims, 2 Drawing Sheets

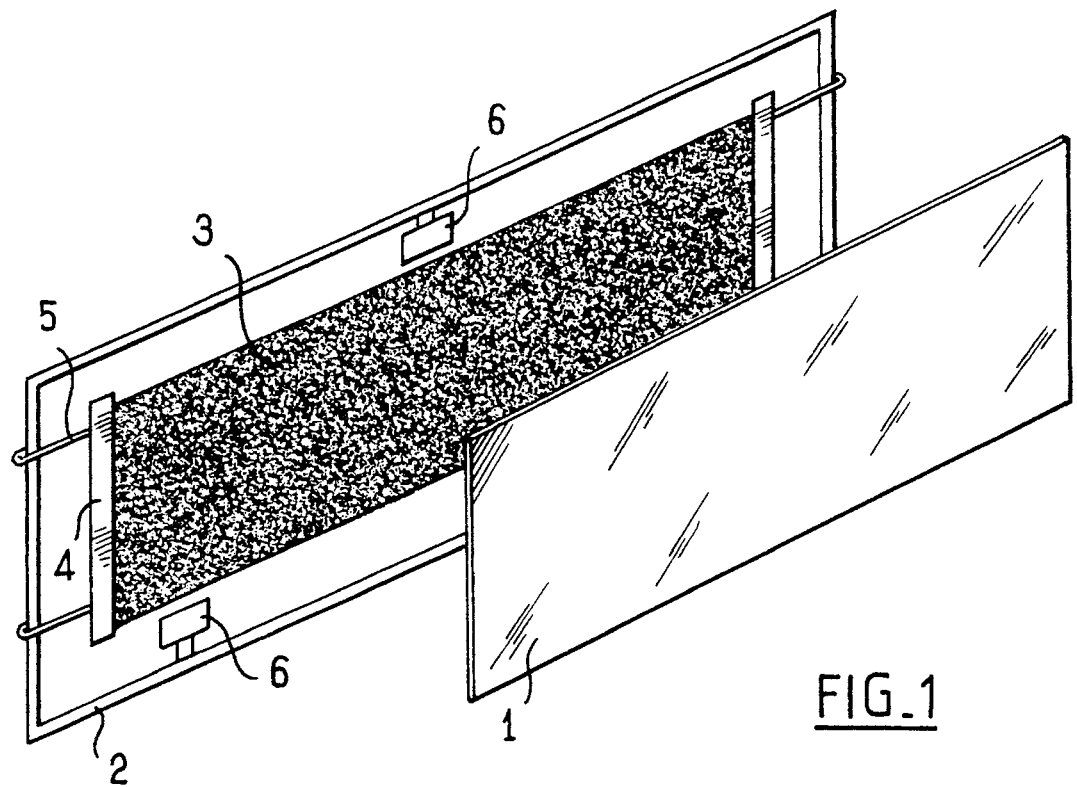
FIG_1
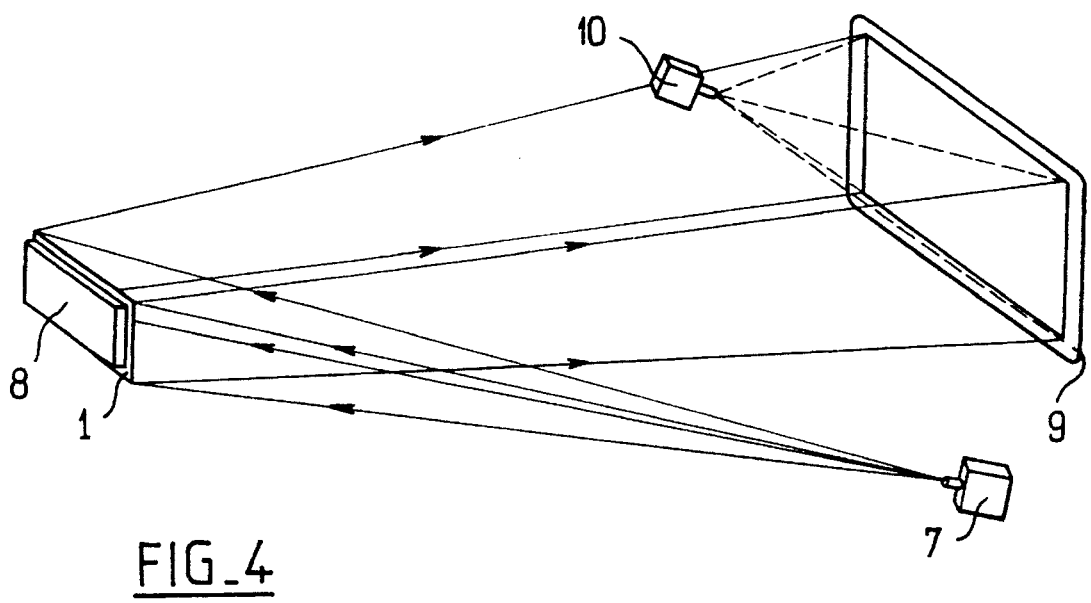
FIG_4

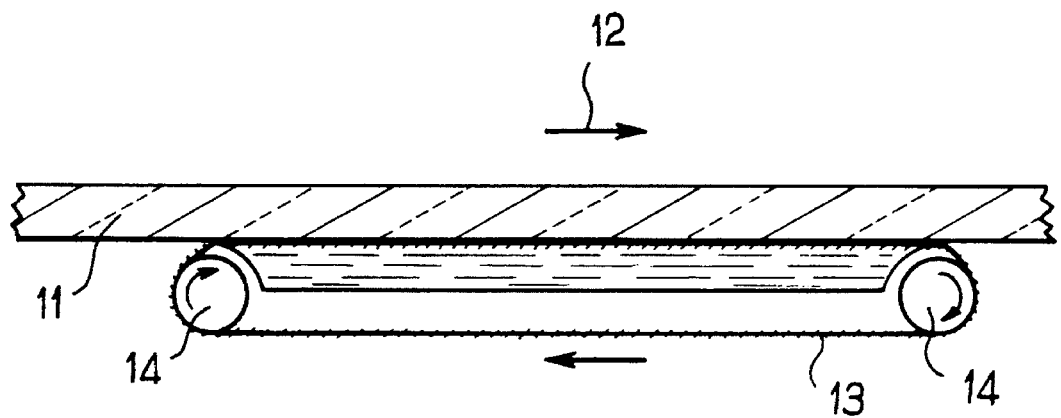
FIG_2
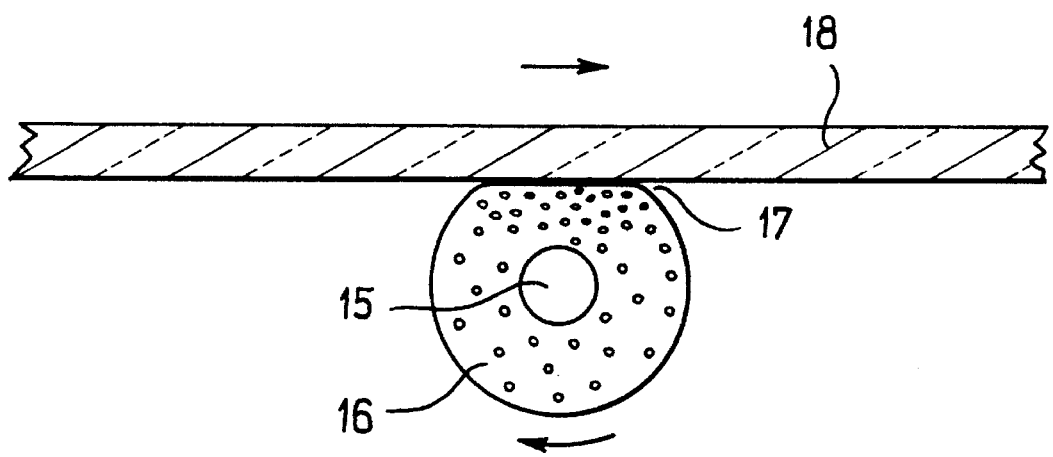
FIG_3

PROCESS AND DEVICE FOR MEASURING OPTICAL QUALITY OF THE SURFACE OF A TRANSPARENT OBJECT BY CONTACT WITH A WETTED FLEXIBLE SURFACE

BACKGROUND OF THE INVENTION

1. Field of the Invention

The invention pertains to measurement of optical quality of the surface of a transparent object. It is especially adapted to measuring the surface of flat glass, especially flat glass which is to be combined with a homologous glass to produce a laminated assembly.

2. Description of the Related Art

Whenever one desires to utilize the optical qualities of a transparent object, it becomes necessary to evaluate the surface characteristics of the object. Thus, if one desires to produce a plain mirror with high precision, to manufacture a heliostat from float glass, it becomes desirable to evaluate the optical quality of the back surface of the glass, which is to be silver plated.

Also, in the fabrication of an automobile laminated windshield, which in a modern car is highly sloped, one will try to combine pairs of sheets whose shapes are such that the transparent plastic material between them has a thickness as constant as possible, so as to avoid a lens effect. In this case it is important to know the irregularities of each surface so that the combination will be beneficial and in order to avoid degradation of the optical quality for each of the sheets of glass.

Also, in the technical field of flat screens, particularly those which utilize liquid crystals, one desires to combine two sheets of thin glass whose facing surface geometries are compatible. Indeed, it is important that the variations of thickness of the sandwiched sheet made of plasma or nematic material be limited.

Methods and devices for measuring by reflection the optical quality of transparent objects, sheets in particular, are well known. U.S. Pat. No. 4,585,343, for example, illustrates a system of continuous evaluation of the inherent flatness of sheets of glass at their output from a sheet hardening furnace. A beam of approximately parallel light is directed perpendicular to the sheet and one controls its variation of convergence after reflection. Such a system provides only gross information, and it is impossible to know what portion of the measured variation of convergence is due to each of the sides or possibly to defects in the glass itself. Moreover, the precision of the method and its power of spatial resolution are inadequate to measure a float glass which has not been subjected to a tempering process.

Optical measurement methods have been developed especially to obtain information on the quality of each of the surfaces of a transparent sheet, independently of one another. French patent FR-B-2,153,817 proposes, in addition to other innovations, a method for measuring the optical quality of a sample by observing the displacement of a luminous beam, the source and the detector being located on the same side. In order to separate the beams reflected by the two sides and to eliminate the one reflected by the back side, an oblique incidence is used and a screen is placed on the path of the second beam. This technique therefore obliges one to use oblique incidence. Another possibility consists in "immersing the second side in a liquid with the same index as the glass."

Another document, EP-A-0,485,043, uses two incident parallel beams and scans the four reflected beams, analysis of the signal allowing one to select the two pencil beams reflected by the front side.

The two preceding methods have the same disadvantages: the measurement is only carried out in one direction and a very precise relative motion (constant speed) is required between the sample to be measured and the apparatus.

The principle of the separation of beams of the preceding methods, due to the necessity of using narrow luminous pencil beams, cannot be applied in ombroscopy, a very interesting gross method because it allows one to detect the most significant defect, whatever its position and direction. Another advantage of ombroscopy is that it does not require relative movement between the sample and the measurement devices.

Another document, U.S. Pat. No. 3,857,637, also proposes to let the sample be moved in its plane and to follow the reflected beam. In order to avoid back reflection, the proposed technique consists in covering the back face of the sample with a coating which absorbs light, such as a dark paint. This is a laboratory technique, however, which is not adapted to fast and non-destructive production inspections.

Several methods for determining if two sheets of glass to be combined with one another with help of a transparent resin have surfaces of complementary shape or not are also known in the prior art.

U.S. Pat. No. 4,837,449 examines parallelism of facing internal surfaces in an assembly of two sheets. The position of a laser beam traversing the assembly is compared to that of the beam which has been successively reflected by the two surfaces that are to be in contact with the inserted resin before traversing the second sheet.

Another document, WO 90/02310, proposes a gap detector which allows one to scan with a laser beam an assembly of two sheets and to study the spots of the reflected beams which overlap when the glasses are parallel and move apart if there is a space anywhere between the two glasses. This method requires a large number of cameras to "auscultate" an entire sheet of glass, otherwise the measurement can only be carried out in one direction, the one perpendicular to the direction of the sweep.

The two preceding methods allow one to give an opinion on the assembly of two transparent sheets which are already combined with one another, but one would like to have a method which allows one to classify sheets in order to know in advance which ones will be capable of being paired while maintaining an acceptable level of quality.

SUMMARY OF THE INVENTION

It is an object of the invention to provide a method for determining the optical quality of the surface of a transparent sheet independent of the quality of the other side or of the plate itself.

It is a further object of the invention to provide a method of measuring the optical quality of the surface of a transparent medium which is global, that is, which pertains to the entire surface and which measures optical defects, whatever their direction.

It is yet a further object of the invention to provide a method and a device for determining the optical quality of the surface of a transparent sheet so as to permit prediction of the optical quality of a laminated final product, after combining said sheet with another one whose characteristics are also known.

The invention proposes a process for measuring the optical quality of the surface of a transparent sheet which has two surfaces which are substantially parallel in which the measurement is made with a light source on the same side of the sheet as the surface to be measured and in which the second surface is in optical contact with another medium in the form of a flexible material wetted by an index liquid. The refractive index of the liquid and that of the transparent sheet need not be identical, but their difference should be between 1 and 20% (based on the index of the sheet), and preferably lower than 15%. In particular, in the case of sheets made of soda lime glass, the index liquid can be water.

By using this process, the evaluation of the optical quality of the front surface alone of a sheet or a transparent medium can be made by all the usual methods for determining the optical quality of a sheet, such as are used for transmission, the only difference being that the light source and the detector are located on the same side of the sheet.

The apparatus for carrying out the invention is simple and inexpensive.

According to the invention, either the light source is localized and the image produced by reflection is evaluated, or the light source generates a narrow beam of light of which the deviations are measured after reflection on the surface to be measured.

Thus, all known processes of measuring the optical quality of glasses are transposable by reflection to allow one, thanks to the invention, to make a measurement of the front surface alone of the transparent sheet.

The invention also envisages application of the process for selection of transparent laminated sheets which are to be assembled by use of a resin, particularly for making glazings that are to be placed on vehicles and especially passenger vehicles and airplanes. It also envisages application of the process for making flat screens. In these cases one determines at each point of the transparent sheets to be assembled an optical value of each of the surfaces that are to face one another, and the values measured at homologous points are combined. Preferably the optical value is the optical power and their combination is an addition.

The process of the invention thus allows one, in contrast to prior methods, to measure each sheet alone and consequently to combine two sheets selected in a manner which will limit the optical defects in transmission of the final glazing.

The invention also proposes a device for implementing the process, which includes a piece of cloth impregnated with the index liquid and held in contact with the surface of the transparent sheet opposite the surface to be measured. Preferably, the cloth is of a dark color, black for example. In the case of a moving sheet, such as a plate of glass or a glass band which is displaced in its plane, a deformable surface made of a flexible or porous material wetted by the index liquid contacts the surface opposite the surface to be measured. The deformable surface is, for example, that of a roller which is rotating and whose surface in contact with the moving sheet has a speed of the same order as that of said sheet.

In a variant, the optical measurement is taken with a point light source which produces the shadow of the surface to be measured on a screen, and a CCD camera evaluates the projected image.

With the technique used for this method of measurement, the necessary devices are quite simple, particularly because no relative displacement of the source and the sample is required.

BRIEF DESCRIPTION OF THE FIGURES

A more complete appreciation of the invention and many of the attendant advantages thereof will be readily obtained as the same becomes better understood by reference to the following detailed description when considered in connection with the accompanying drawings, wherein:

FIG. 1 shows a transparent sheet and the impregnated fabric with which it will be in contact;

FIG. 2 and FIG. 3 each shows a device in which the impregnated or wetted flexible or porous material is moving with the sheet itself; and FIG. 4 shows an installation for the ombroscopy measurement of the front side of a transparent sheet.

DETAILED DESCRIPTION OF THE PREFERRED EMBODIMENTS

All known methods for measuring the flatness of the surface of a transparent sheet use the same techniques as those developed for measuring in transmission the optical quality of transparent sheets. When these techniques are used without any special precautions the measurement provides a gross value which combines defects of three sources: those which come from deviations of flatness of each of the two surfaces and those which derive from the heterogeneities of the composition of the transparent material constituting the sheet.

In order to limit the information to that coming from the front side of the sample, one must eliminate the light reflected on the second side. One thereby simultaneously eliminates not only the action of the back reflecting surface but also the effect of defects in the sheet itself. The study of the prior art showed the difficulties related to occultation by a screen of the beam reflected by the second side of the sample. As for the known methods which consist in placing the second side in contact with an index liquid, they are most frequently described without a description of any practical implementation.

The principle of the invention is the following:

A porous material such as a foam with open pores, or a fabric, or at least a material with a flexible surface, is impregnated or its surface is simply wetted by an index liquid whose index of refraction is similar to that of the sheet to be tested. One then establishes a close contact between the measurement area of the sheet and the surface wetted with the index liquid. In this way the measuring light rays which have penetrated the sheet at the time of measurement of the optical quality, instead of being reflected by the second surface when they strike it, continue their trajectory into the index liquid and its support material where they are diffused in all directions and—at least partially—absorbed. Even if the support material is not very absorbing, when one is measuring the deviation of the narrow beam of light, the fact that at the time of their diffusion the rays undergo a random change of direction is enough to neutralize the second reflection.

On the other hand, if one uses an ombroscopic method of the kind described for transmission measurement in U.S. Pat. No. 5,016,099 or U.S. Pat. No. 5,146,282, the contrast of the observed image is degraded by any parasitic light and, if the support material of the index liquid is not of a dark color, the measurement could be more difficult for it. That is why, in this case, one tries to use a material which is preferably colored black.

The choice of the index liquid is made as traditionally done in the laboratory. Thus, for sheets of soda lime glass (index of refraction 1.52), one will choose, for example, dimethyl phthalate. For a sheet of methyl methacrylate (PMMA), vaseline oil, for example, will be used.

But when techniques of the invention were used, it was discovered, unexpectedly, that even with a liquid whose index of refraction deviates appreciably from that of the sheet, the effect of reflection on the back side of the sheet was eliminated in the measurement when the devices of the invention were used.

The latter are shown in the figures.

FIG. 1 shows a glass sheet 1. It is desired to measure the optical quality of the side of sheet 1 directed toward the observer. Behind the sheet 1, whose orientation in space does not matter (it is vertical in this case), is placed, parallel to it, a frame 2 made of metal, for example.

A dark colored fabric 3 is held in the frame 2. The fabric is held tight at its ends in rods 4 which are attached by elastic devices 5 to frame 2. The fabric is impregnated with the index liquid. When the fabric is vertical, one may place along its upper edge a row of sprinklers (not shown) which distributes the liquid over its entire length. Bubbles of air remaining on the liquid/transparent material interface should be avoided.

The choice of fabric plays an important role. It should not have too fine a texture, so that air can escape through the mesh of the fabric. Also, to ensure contact between the sheet and the index liquid sufficient to optically couple the two, the fabric must be evenly pressed over its entire surface. The nature of the fabric must allow such an even pressure.

In order to ensure adequate even pressure to provide such contact, planar thrust pieces 6 are mounted to the frame at regular intervals. The plane of each of the thrust pieces is located slightly behind the plane of the fabric when it is unstressed. A gap of 2 mm, for example, is appropriate. The pane is then pressed onto the fabric until the pane contacts the thrust pieces. When sheet 1 rests on thrust pieces 6, it is assured that the sheet/fabric contact, and therefore the sheet/index liquid contact, is complete.

Ombroscopic measurements may be made using the device of FIG. 1. The installation shown in FIG. 4 includes all the components of U.S. Pat. No. 5,146,282.

Referring to FIG. 4, a projector 7 is equipped with a diaphragm having a diameter which will allow one at the level of sheet 1 to have a resolving power which is adjusted to the dimensions of defects which one wishes to measure (see U.S. Pat. No. 5,146,282). Projector 7 is located, for example, 4 meters away from sheet 1. The latter is provided at its back with frame 2 having fabric 3 of FIG. 1, the whole assembly being shown schematically at 8.

The reflection from the front side of sheet 1 is projected onto screen 9 which is also located 4 meters away from sheet 1. The screen is observed through the CCD camera 10. At each point of the screen, the measured illumination is compared to a reference illumination stored in memory and based on a prior measurement using a sheet of excellent quality, for example a sheet of mechanically polished glass. This "zero measurement" is used to eliminate the effect of illumination variations caused by the point source. The variation of measured illumination with respect to the reference value is directly proportional to the positive optical power (more light) or negative optical power (less light) of the surface unevenness of sheet 1. Reference standards are used to calibrate the measurement method.

Tests were carried out with the device of FIG. 1, in which the value of the index of refraction of the index liquid was gradually separated from the value of the index of the sheet, by using different liquids. It was determined that a difference of 20% for the index of refraction for the reference liquid as compared to that of the sheet would not disturb the measurements. For example, using a sheet of industrial glass (n=1.52), pure water (n =1.33) was successfully used as an index liquid, which is of obvious practical benefit.

FIG. 2 and FIG. 3 show devices in accordance with the invention which have been particularly adapted to measurement of a moving band of glass such as float glass, on a production line as well as sheets of cut glass which move forward before being paired in order to constitute the two components of a laminated automobile glazing.

In FIG. 2 the sheet 11 travels in the direction of arrow 12. Beneath the sheet a continuous belt of fabric 13 is driven by rollers 14. In the upper part of its path the fabric belt 13 is in contact with water and cooperates with the lower side of the sheet 11. The speeds of the sheet and fabric belt are similar. The optical measurement is made from above the sheet using one of the traditional methods described earlier.

A variant of the preceding device is shown in FIG. 3. A roller 15 whose axis is parallel to the sheet and perpendicular to its direction of travel is provided on its periphery with a spongy sleeve 16 whose surface is soft. A device which is not shown moistens the surface of the sponge 16 with the index liquid just before it comes in contact at 17 with the lower surface of the sheet 18.

A measurement device based on that of U.S. Pat. No. 5,016,099 allows one to carry out a complete measurement of the upper surface of sheet 18 whose lower side is in contact with the moistened soft surface.

The measurement technique of the invention also allows one to select from among the sheets of glass those which it is convenient to pair in order to obtain satisfactory optical quality in transmission following lamination.

The preceding measurement method of FIG. 4 allows one to determine the optical power at each point of the surface of each sheet. Because of the fact that, in general, the inserted resin, most frequently polyvinyl butyral, is homogeneous and introduces no optical defects, only its variations of thickness due to the quality of the surfaces facing one another play a role in the optical quality of the assembled product. It thus suffices to add the measured power values at each homologous point on the two surfaces in order to obtain the "map" of the expected optical powers in transmission for the assembled glazing. If at one place the expected value exceeds a limit which one has established, the operation stops and one thus avoids proceeding on in vain to costly industrial operations. Moreover, it is possible to attempt a new match in which each of the sheets will be combined with a sheet which has a different distribution of defects which would allow one to achieve a better result by the new pairing.

Obviously, numerous modifications and variations of the present invention are possible in light of the above teachings. It is therefore to be understood that the invention may be practiced otherwise than as specifically described herein.

What is claimed as new and desired to be secured by Letters Patent in the United States is:

1. A process for measuring the optical quality of one surface of a transparent sheet which has another surface approximately parallel to said one surface, comprising the steps of:

causing light from a light source to reflect from said one surface;

using a measuring device to measure the reflected light; and applying to the another surface, during said causing step, a flexible material wetted by an index liquid so as to substantially eliminate light reflections from the another surface.

2. The process of claim 1 wherein said light source and said measuring device are both on the same side of the sheet as said one surface.

3. The process of claim 1 wherein the index of refraction of the index liquid and the index of refraction of the transparent sheet are not identical and wherein a difference between said indexes is from 1 to 20% of the index of refraction of the sheet.

4. The process of claim 3 wherein said difference is from 1 to 15%.

5. The process of claim 3 wherein said sheet is made of soda lime glass and the index liquid is water.

6. The process of claim 1 wherein said light source produces a narrow beam of light, wherein said measuring step comprises the step of measuring deviations in the reflected light.

7. The process of claim 1 wherein said applying step comprises evenly pressing the flexible material to the another surface with sufficient force to optically couple the index liquid with the another surface.

8. The process of claim 7 including the step of moving the transparent sheet and the optical material at substantially the same speed during said applying step.

* * * * *

UNITED STATES PATENT AND TRADEMARK OFFICE
CERTIFICATE OF CORRECTION

PATENT NO. : 5,602,648
DATED : February 11, 1997
INVENTOR(S) : Paul H. GUERING, et al.

It is certified that error appears in the above-indentified patent and that said Letters Patent is hereby corrected as shown below:

On the title page, Item [22], the filing date, should read:

--Mar. 31, 1995--

Signed and Sealed this

Thirteenth Day of May, 1997

Attest:

BRUCE LEHMAN

Attesting Officer

Commissioner of Patents and Trademarks